(12) United States Patent
Schampers et al.

(10) Patent No.: US 7,615,745 B2
(45) Date of Patent: Nov. 10, 2009

(54) METHOD FOR SEPARATING A MINUTE SAMPLE FROM A WORK PIECE

(75) Inventors: Rudolf Johannes Peter Gerardus Schampers, Belfeld (NL); Theodorus Adrianus Petrus Verkleij, Overasselt (NL); Hendrik Siewerd Venema, Eindhoven (NL)

(73) Assignee: FEI Company, Hillsboro, OR (US)

( * ) Notice: Subject to any disclaimer, the term of this patent is extended or adjusted under 35 U.S.C. 154(b) by 327 days.

(21) Appl. No.: 11/775,121

(22) Filed: Jul. 9, 2007

(65) Prior Publication Data
US 2008/0042058 A1    Feb. 21, 2008

(30) Foreign Application Priority Data
Jul. 10, 2006    (EP)    .................................. 06116886

(51) Int. Cl.
*H01J 37/305* (2006.01)
*H01J 37/20* (2006.01)
*G01N 1/28* (2006.01)

(52) U.S. Cl. .................. 250/304; 250/307; 250/442.11
(58) Field of Classification Search ................ 250/304, 250/307, 309, 442.11, 311, 492.21
See application file for complete search history.

(56) References Cited

U.S. PATENT DOCUMENTS

| 5,270,552 A | 12/1993 | Ohnishi et al. |
| 6,452,174 B1 | 9/2002 | Hirose et al. |
| 6,960,765 B2 | 11/2005 | Tomimatsu et al. |
| 7,009,188 B2 * | 3/2006 | Wang .................... 250/442.11 |
| 7,173,253 B2 | 2/2007 | Aiba |
| 7,268,356 B2 * | 9/2007 | Shichi et al. ........... 250/492.21 |
| 7,301,146 B2 | 11/2007 | Tomimatsu et al. |
| 7,408,178 B2 * | 8/2008 | Tappel ................... 250/492.21 |

* cited by examiner

*Primary Examiner*—Jack I Berman
(74) *Attorney, Agent, or Firm*—Scheinberg & Griner, LLP; Michael O. Scheinberg; David Griner

(57) ABSTRACT

The invention pertains to a method for separating a minute sample (1) from a work piece (2). Such a method is routinely used in the semiconductor industry to obtain samples from wafers to be inspected in a TEM. It occurred to the inventor that approximately 20% of the obtained samples could not be properly finished (thinned) due to a misalignment of specimen carrier (6) and sample. It turned out that this misalignment is caused by the specimen carrier contacting the sample prior to welding. By not contacting the sample while welding, but leaving a small gap between specimen carrier and sample, this misalignment is avoided. To avoid movement of the specimen carrier during welding, due to e.g. vibration, the specimen carrier can be landed on the wafer on a position (8) close to the sample.

20 Claims, 3 Drawing Sheets

METHOD FOR SEPARATING A MINUTE SAMPLE FROM A WORK PIECE

Figure 1A:
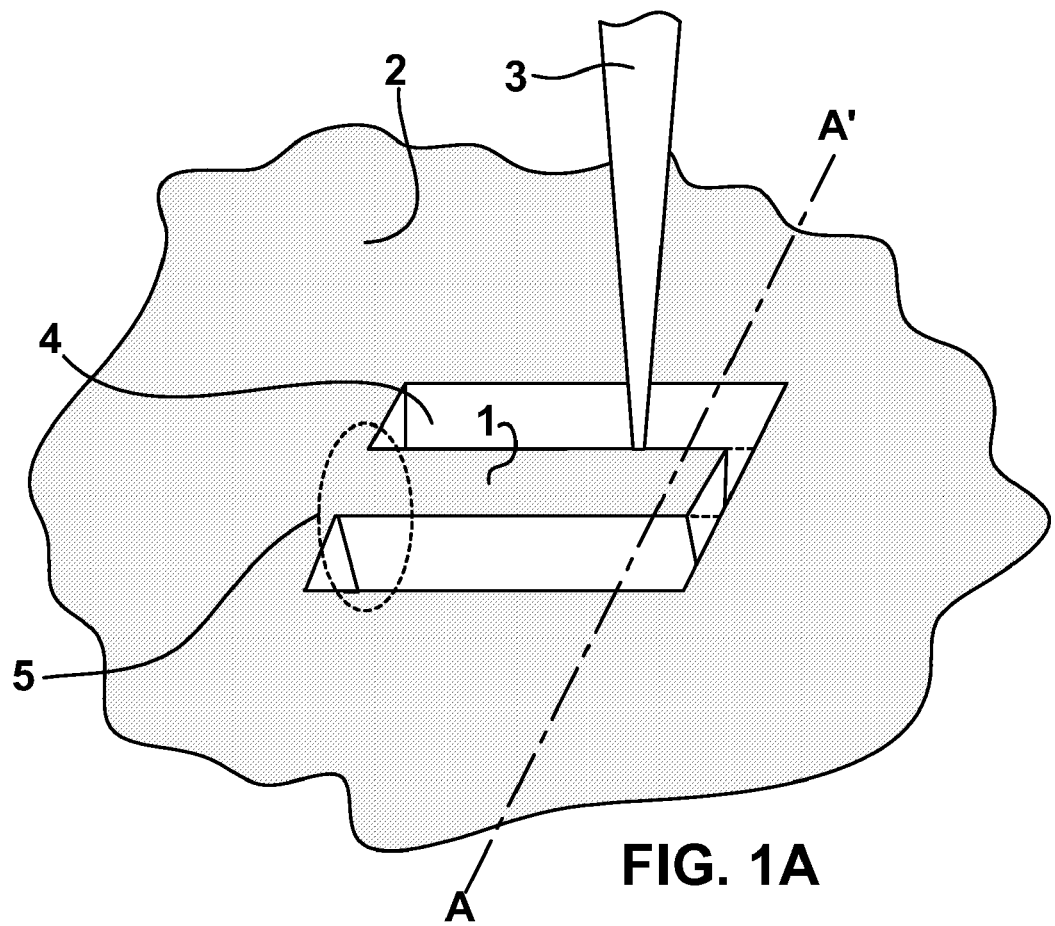

The invention relates to a method for separating a minute sample from a work piece and attaching said sample to a specimen carrier, the method comprising:
- Focussing a beam onto the work piece so that material is removed from the work piece,
- Connecting the specimen carrier to the sample by depositing a continuous body of material on sample and specimen carrier, and
- Completely separating the sample from the work piece.

Such a method is known from U.S. Pat. No. 5,270,552.

Such a method is used in the semiconductor industry, where minute samples are taken from semiconductor wafers for analysis in e.g. a Transmission Electron Microscope (TEM).

The analysis of samples taken from semiconductor wafers in a TEM is known per se. As known to the person skilled in the art the samples to be analysed in a TEM must be extremely thin, e.g. 50 nm.

The size of the samples analyzed in a TEM are nowadays e.g. 10 μm long (originally in a direction parallel to the wafer surface), 5 μm wide (originally in a direction perpendicular to the wafer surface) and 50 nm thick, although other sizes may be used.

In the known method a sample is separated from a work piece in the form of a wafer by irradiating the wafer with a focused beam of e.g. energetic ions, such as a beam of Ga$^+$ ions with an energy of 30 keV. Where the beam impinges upon the wafer, material is removed. By scanning the beam over the wafer (by deflecting the beam using e.g. electrostatic or magnetic deflectors) a pattern can be dug into the surface of the wafer.

The sample is separated from the wafer by e.g. scanning the beam over the wafer in such a way that the portion of the wafer to be separated is surrounded by a trench, while at the same time or at a later time undercutting the sample, so that sample is completely separated from the wafer.

In the known method the sample is connected to a specimen carrier before it is completely separated from the wafer.

The known method describes that connecting the sample to the specimen holder, also named welding, involves the subsequent steps of:
- contacting the sample and the specimen carrier before the sample is completely separated from the wafer,
- welding the sample and specimen carrier together by e.g. the deposition of a material, and
- completely separating wafer and sample, leaving the sample attached to the specimen carrier.

The sample so separated is not yet thin enough for analysis in a TEM. Often the sample has, prior to complete separation, the shape of a prism with a length of e.g. 10 μm, in which the triangular cross-section has a dimension of e.g. 5 μm at the surface of the wafer tapering to zero at a depth corresponding to a depth of 5 μm below the surface of the wafer.

The known method therefore describes that the sample may after separation be processed so as to have a shape suitable for analysis.

A known method of thinning the sample is by milling the sample with an ion beam. For proper thinning the orientation of the sample with respect to the specimen carrier must be known so as to align the sample to the ion beam used for milling. Improper alignment might e.g. lead to loss of material to be examined.

It has come to the attention of the inventor that, due to a misalignment of the sample with respect to the specimen carrier, approximately 20% of the samples are not thinned properly and are lost for further analysis. Obviously this leads to extra time needed to obtain additional samples, extra sites on the wafer being damaged due to the digging out of samples and the loss of useful information. This is clearly disadvantageous to the users of the process.

It is an object of the invention to provide a method that reduces the number of samples lost due to misalignment between sample and specimen carrier after welding.

To that end the method according to the invention is characterised in that during connection the specimen carrier and the sample are separated by a gap, as a result of which the specimen carrier does not displace the sample during connection.

The invention is based on the inventors insight that, as a result of the specimen carrier contacting the sample prior to welding, the orientation of the sample may be changed due to the forces that the specimen carrier exerts on the sample, as a result of which the orientation of the sample with respect to the specimen carrier is changed.

The invention is further based on the insight that, for a proper weld to form, it is not necessary that the two parts to be welded together (the sample and the specimen carrier) must contact each other: it is sufficient that they are kept at close proximity to each other so that the continuous body of material can be deposited upon them.

It is remarked that the sample can be completely separated from the work piece by surrounding the sample with a trench and by completely undercutting the sample, as described in the known method. However, also other ways of separating the sample are used, such as breaking the sample from the work piece. The latter method can be used when there is a connecting part at a side of the sample (because the trench does not completely surround the sample) or when there is a connecting part at the bottom of the sample (because the sample is not or not completely undercut).

In an embodiment of the method according to the invention the continuous body of material is formed by depositing material from a material in the gas or vapour phase.

Depositing material from a material in the gas or vapour phase is a known method. An advantage of this method is that no forces are exerted upon the two bodies being welded together, this in contrast with a method in which the bodies are joined by e.g. electrostatic force or by applying e.g. glue. Therefore when depositing material from the gas or vapour phases the welding process itself does not disturb the orientation of the sample with respect to the specimen carrier.

In a further embodiment of the method according to the invention the deposition is induced by an electron beam (Electron Beam Induced Deposition or EBID), an ion beam (Ion Beam Induced Deposition or IBID) or a laser beam (Laser Induced Deposition or LID).

EBID, IBID and LID are known per se. EBID, IBID and LID induce a localized deposition of material. A localized deposition is advantageous to avoid material build-up at unwanted places, such as in the trench milled previously between sample and work piece. Especially EBID and IBID, using beams that can be focussed to a diameter of much less than 1 μm are suited to form a localized body of deposited material (a weld) with a dimension fit for the minute sample sizes presently used in e.g. the semiconductor industry.

In another embodiment of the method according to the invention the specimen carrier contacts the work piece while the material forming the continuous body of material is deposited.

By contacting the specimen carrier to the work piece unintended movements of that part of the specimen carrier to with the sample is to be connected, e.g. due to vibrations, are strongly reduced. It is remarked that while forming the connection the sample is still connected to the work piece, and thus by supporting the specimen carrier on the work piece, relative movement of the sample and the specimen carrier are suppressed as well.

In a further embodiment of the method according to the invention the shape of the specimen carrier is modified with a focused beam prior to connecting the specimen carrier to the sample.

In order for the specimen carrier to contact the work piece while keeping a small clearance to the sample, the specimen carrier must be shaped appropriate.

In a yet further embodiment of the method according to the invention the sample is separated from the work piece in a vacuum chamber, and the modification of the shape of the sample carrier takes place in that same vacuum chamber.

As known to the person skilled in the art milling with e.g. an ion beam takes place in vacuum, or in an environment with a very low pressure. This is true for the milling of the trench in the work piece so as to free the sample from the work piece, as well as for milling the specimen carrier to a shape appropriate for contacting the work piece while keeping a small gap to the sample.

In a still further embodiment of the method according to the invention the focused beam used for the modification of the shape of the specimen carrier is an electron beam, an ion beam or a laser beam.

In a yet further embodiment of the method according to the invention the focused beam used for the shaping of the specimen carrier is also used for the formation of the continuous body of material.

In other further embodiment of the method according to the invention the focused beam used for the shaping of the specimen carrier is the same focused beam used for the removing of material from the work piece In another embodiment of the method according to the invention the sample is completely separated form the work piece by breaking it from the work piece.

The invention will be elucidated on the basis of figures, where identical reference numerals indicate corresponding elements.

Figure 1B:
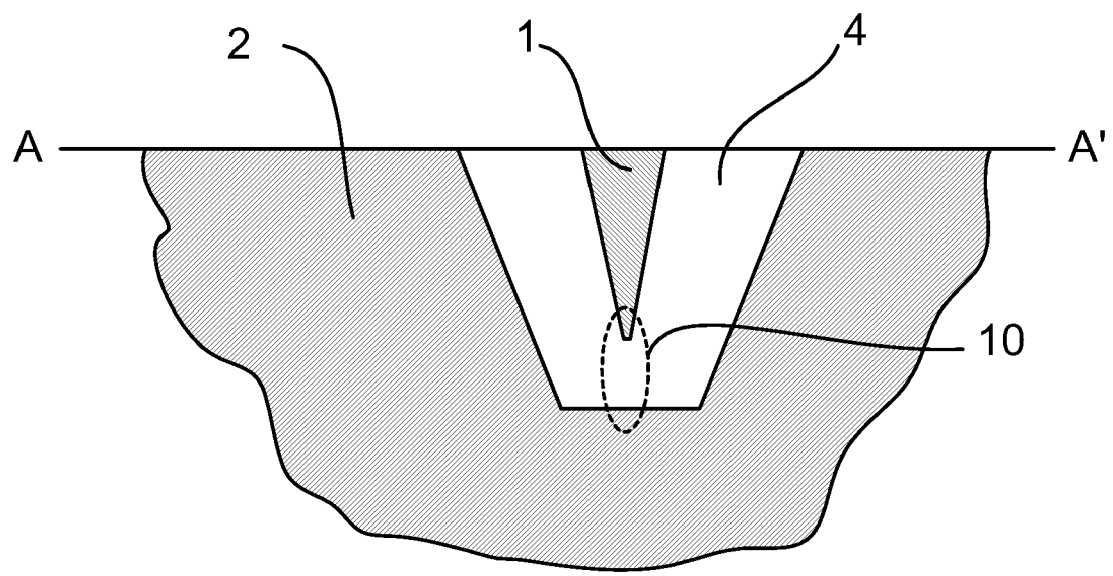
Figure 2:
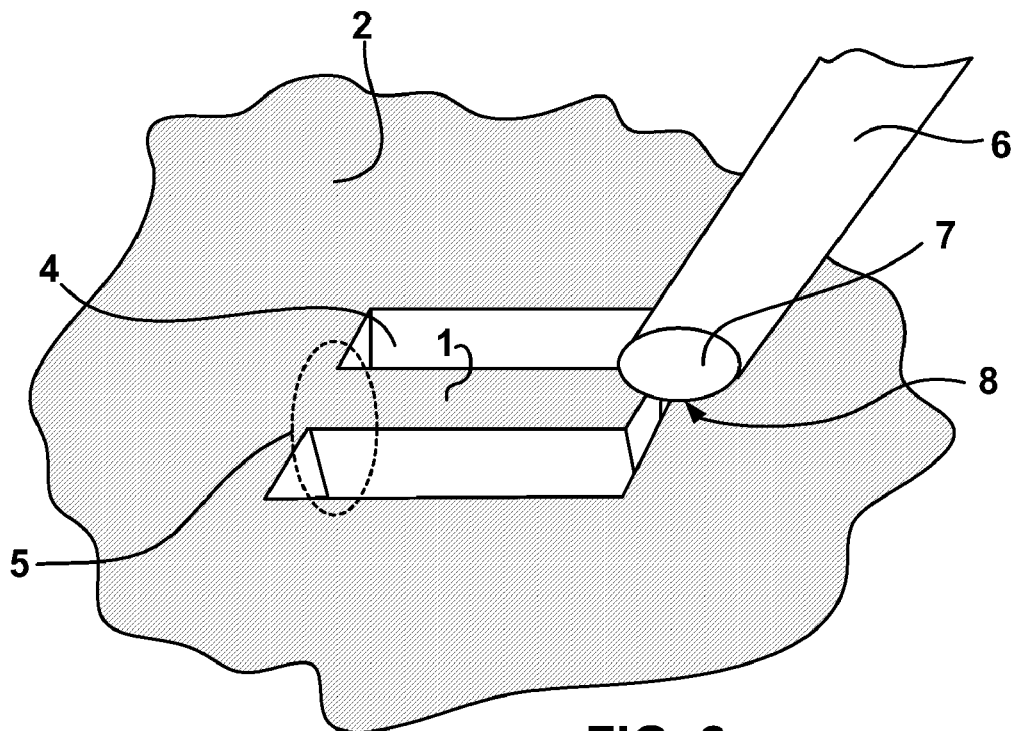
Figure 3:
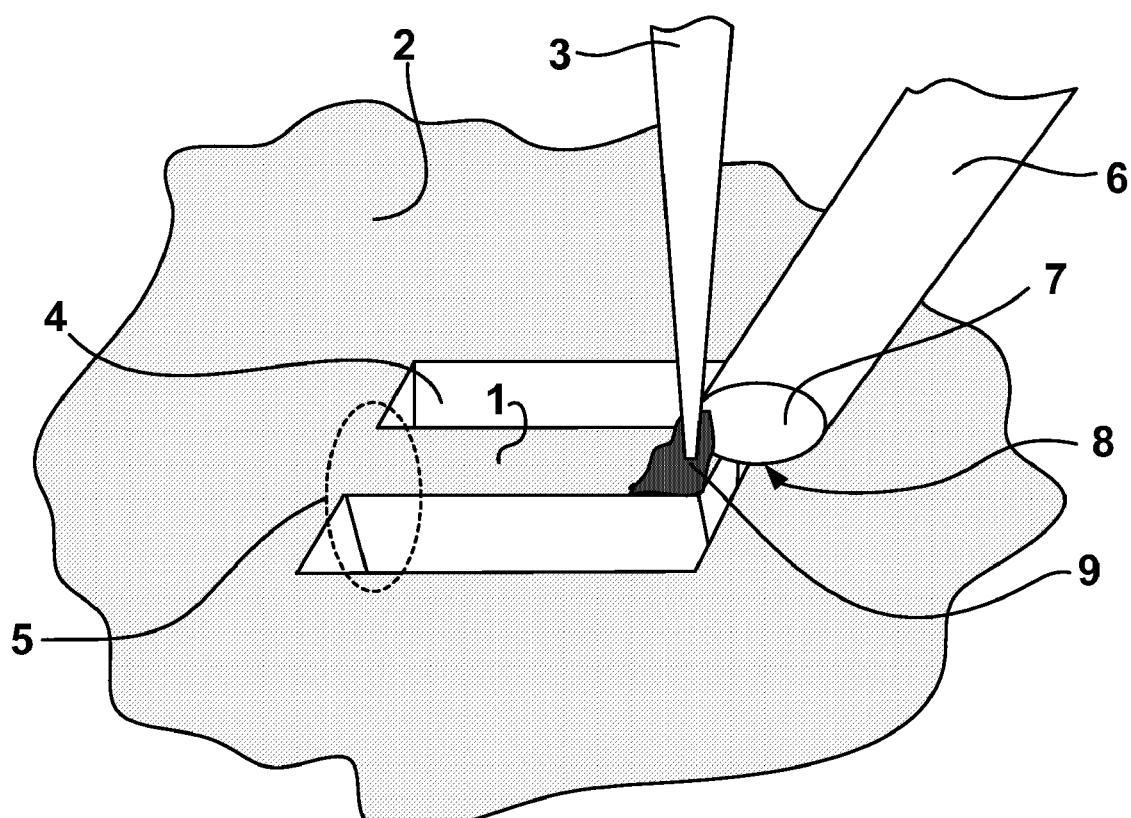
Figure 4:
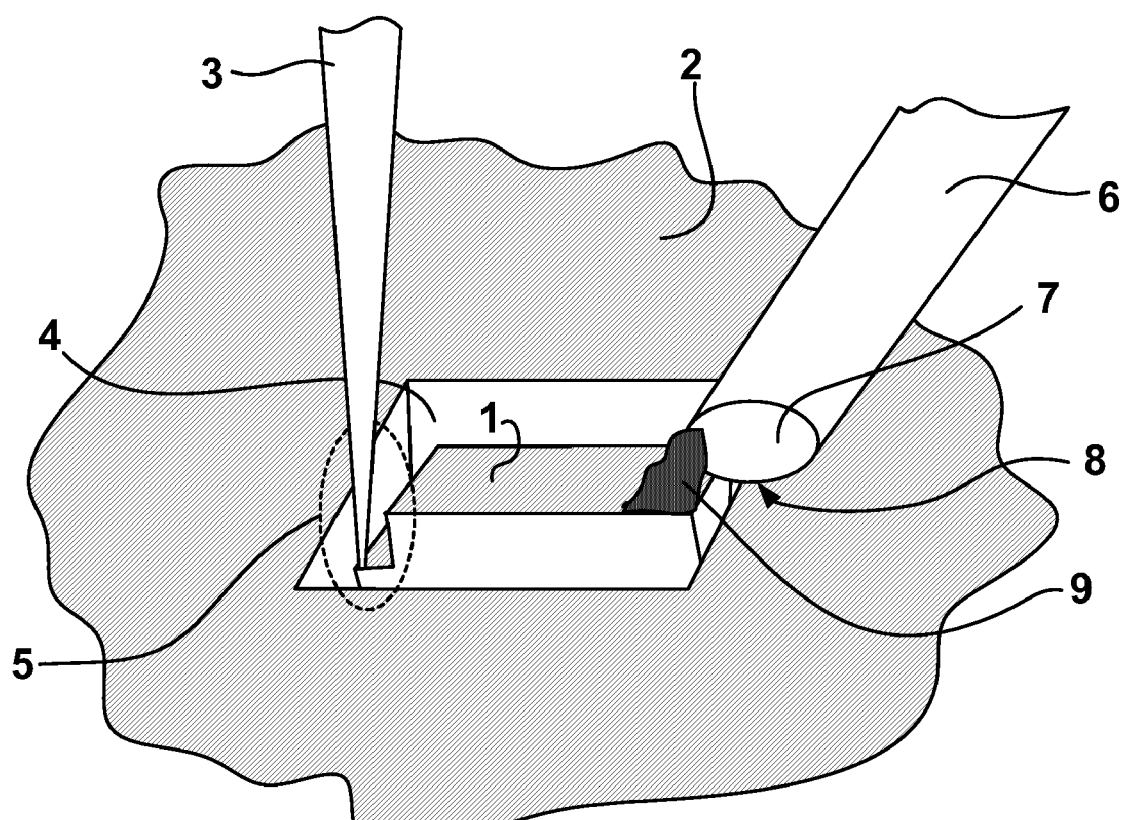

To this end:

FIG. 1A depicts schematically a view of a wafer, where material is removed by an ion beam, FIG. 1B depicts schematically a cross-section of the wafer shown in FIG. 1A along line AA', FIG. 2 depicts schematically a view of the specimen carrier positioned on the wafer just prior to welding FIG. 3 depicts schematically a view of the sample being welded to the specimen carrier, and FIG. 4 depicts schematically a view of the sample being completely separated from the wafer.

FIG. 1A shows a schematic view of a wafer, where material is removed by an ion beam.

Wafer 2 is irradiated with an ion beam 3, whereby material is removed from wafer 2 and a trench 4 is formed round sample 1. At this stage, before sample 1 is welded to a specimen carrier, sample 1 is not completely separated from the wafer, but a connecting part in region 5 is kept intact.

FIG. 1B shows a schematic cross-section of the wafer along line AA'. As shown sample 1 is free from the bottom of the trench 4 shown in region 10.

It is remarked that in FIG. 1B a completely undercut sample is shown. It is however not necessary to completely undercut the sample: as mentioned earlier the sample can be completely separated form the wafer by breaking it from the wafer, e.g. because there is a thin wall connecting the bottom of the trench and the underside of the sample in region 10.

It is further remarked that, although the milling process takes place at very low pressures (typically 1-10 mbar), small amounts of certain gasses can be injected at this (partial) pressure to increase the milling speed of the ion beam.

FIG. 2 shows a schematic view of the sample being welded to the specimen carrier.

FIG. 2 can be thought to be derived from FIG. 1A. The specimen carrier 6 has the form of a tapering cylinder with a truncated end 7. The specimen carrier is moved with a manipulator (not shown) with which it is connected to a position on the wafer, so that it rests with its truncated end 7 on wafer 2 at position 8. Position 8 is close to trench 4 and in line with the sample 1. Thereby the distance between the truncated end 7 of the specimen carrier 6 and the sample 1 is sufficiently small to be filled/covered with a material to be deposited from a material in the gas or vapour phase.

It is to be mentioned that it is not necessary to do both the milling of the trench, the shaping of the specimen carrier and/or the deposition of the material with the same focused beam. However, as known to the person skilled in the art, the same beam can be used for both milling and depositing material by changing the current density in the focus of the beam where it impinges on the wafer or specimen carrier, and/or by changing the pressure or composition of the gas or vapour in the vicinity of the focus of the beam. Both electron and ion beams are known to do either deposition or milling, depending on current density and gas/vapour composition and pressure. Also ablation with a laser is possible, as well as deposition with a laser beam. Therefore all three types of beams are in principle suited to perform milling and/or deposition, and certain steps of the method can even be performed simultaneously.

It is further to be mentioned that the specimen carrier 6 depicted here strongly resembles the needle-like structures used in the prior art as specimen carriers, but with a cut-off end part. In experiments this shape showed to be very convenient for the method according to the invention, while the shape can easily be attained by cutting the end from a needle as used in e.g. the known method with an ion beam, such as ion beam 3.

It is remarked that the shaping of the specimen carrier can take place 'in situ', that is in the same apparatus where the wafer is processed and the sample is extracted, as well as 'ex situ'.

Further it is remarked that this method can also be performed in an apparatus where e.g. an ion beam is used for milling and for depositing material, while an electron beam and secondary electron detectors are used to monitor the progress of the process according to the method.

It is mentioned that the thinning of the sample can take place at several locations: the sample can be thinned while it is still connected to the wafer, it can be thinned in-situ in the apparatus where the sample is separated from the wafer, or the thinning can take place in another apparatus. Also combinations of these possibilities are envisaged.

We claim as follows:

1. Method for separating a minute sample from a work piece and attaching said sample to a specimen carrier, the method comprising Focussing a beam onto the work piece so that material is removed from the work piece, Connecting the specimen carrier to the sample by depositing a continuous body of material on sample and specimen carrier, and Completely separating the sample from the work piece, Characterized in that During connection the specimen carrier and the sample are separated by a gap, as a result of which the specimen carrier does not displace the sample during connection.

2. Method according to claim 1 in which the continuous body of material is formed by depositing material from a material in the gas phase or the vapour phase.

3. Method according to claim 2 in which the deposition is induced by an electron beam (Electron Beam Induced Deposition or EBID), an ion beam (Ion Beam Induced Deposition or IBID) or a laser beam (Laser Induced Deposition or LID).

4. Method according to claim 1 in which the specimen carrier contacts the work piece while the material forming the continuous body of material is deposited, as a result of which the relative position of specimen carrier and the sample connected to the work piece is kept stable.

5. Method according to claim 4 in which the shape of the specimen carrier is modified with a focused beam prior to connecting the specimen carrier to the sample to a shape suitable for contacting the work piece while coming in close proximity, but not in contact with the sample.

6. Method according to claim 5 in which the sample is separated from the work piece in a vacuum chamber, and the modification of the shape of the specimen carrier takes place in that same vacuum chamber.

7. Method according to claim 6 in which the focused beam used for the modification of the shape of the specimen carrier is an electron beam, an ion beam or a laser beam.

8. Method according to claim 7 in which the focused beam used for the shaping of the specimen carrier is also used for inducing the formation of the continuous body of material.

9. Method according to claim 7 in which the focused beam for the shaping of the specimen carrier is the same focused beam used for removing material from the work piece.

10. Method according to claim 1 in which the sample is completely separated from the work piece by breaking the sample from the work piece.

11. Method according to claim 2 in which the specimen carrier contacts the work piece while the material forming the continuous body of material is deposited, as a result of which the relative position of specimen carrier and the sample connected to the work piece is kept stable.

12. Method according to claim 3 in which the specimen carrier contacts the work piece while the material forming the continuous body of material is deposited, as a result of which the relative position of specimen carrier and the sample connected to the work piece is kept stable.

13. Method according to claim 11 in which the shape of the specimen carrier is modified with a focused beam prior to connecting the specimen carrier to the sample to a shape suitable for contacting the work piece while coming in close proximity, but not in contact with the sample.

14. Method according to claim 12 in which the shape of the specimen carrier is modified with a focused beam prior to connecting the specimen carrier to the sample to a shape suitable for contacting the work piece while coming in close proximity, but not in contact with the sample.

15. Method according to claim 2 in which the sample is completely separated from the work piece by breaking the sample from the work piece.

16. Method according to claim 3 in which the sample is completely separated from the work piece by breaking the sample from the work piece.

17. Method according to claim 4 in which the sample is completely separated from the work piece by breaking the sample from the work piece.

18. Method according to claim 5 in which the sample is completely separated from the work piece by breaking the sample from the work piece.

19. Method according to claim 6 in which the sample is completely separated from the work piece by breaking the sample from the work piece.

20. Method according to claim 7 in which the sample is completely separated from the work piece by breaking the sample from the work piece.

* * * * *